United States Patent [19]

Shewchuk

[11] Patent Number: 5,782,845
[45] Date of Patent: Jul. 21, 1998

[54] TROCAR SITE SUTURING DEVICE

[76] Inventor: Dwight Shewchuk, 4343 Gloster Rd., Dallas, Tex. 75220

[21] Appl. No.: 868,366

[22] Filed: Jun. 3, 1997

Related U.S. Application Data

[63] Continuation-in-part of Ser. No. 688,864, Jul. 31, 1996, abandoned.

[51] Int. Cl.$^6$ .................................................. A61B 17/04
[52] U.S. Cl. .......................................... 606/144; 606/139
[58] Field of Search .................................. 606/139, 144, 606/146, 147

[56] References Cited

U.S. PATENT DOCUMENTS

| 5,449,367 | 9/1995 | Kadry ....................... | 606/139 |
| 5,462,560 | 10/1995 | Stevens ..................... | 606/139 |
| 5,472,556 | 12/1995 | de la Torre ................. | 606/144 |
| 5,480,405 | 1/1996 | Yoon ........................ | 606/147 |

OTHER PUBLICATIONS

Literature on Endo Close AutoSuture device by United States Surgical Corporation, 1994.

*Primary Examiner*—Gary Jackson
*Attorney, Agent, or Firm*—W. Thomas Timmons; Timmons & Kelly

[57] ABSTRACT

An apparatus (10) for suturing wounds (12) in a patient includes a first elongated hollow body (14) having a bore (16) therethrough. The hollow body (14) has a first end (18) adapted to receive a suturing element (20) and a second end (22) adapted to penetrate a tissue layer (24). A second elongated member (28) has a first end (30) and a second end (32) with an aperture (34). A first alignment device (38) is disposed with the first end (18) of the hollow body (14) and a second, cooperating alignment device (40) is disposed with the first end (30) of the second elongated member (28) such that the joining of the first alignment device (38) and the second alignment device (40) holds the hollow body bore (16) in alignment with the second elongated member aperture (34).

26 Claims, 2 Drawing Sheets

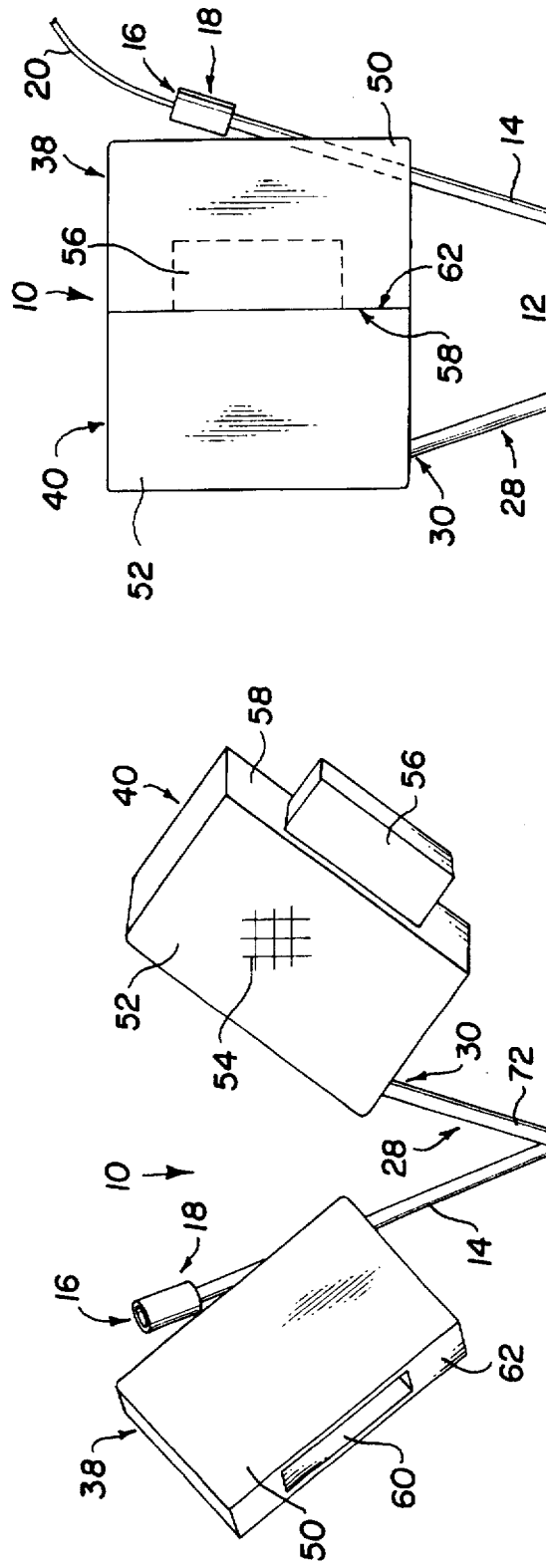
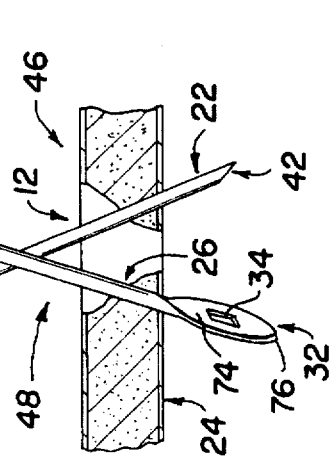
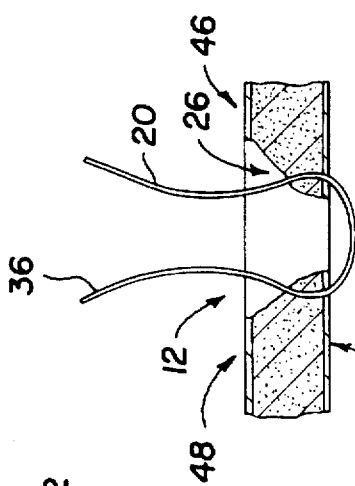
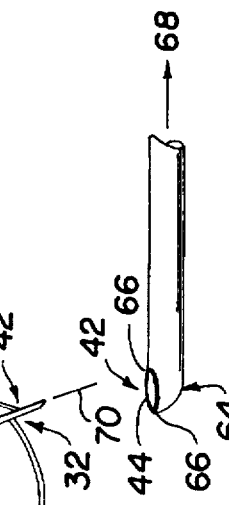
Fig. 1
Fig. 2
Fig. 3
Fig. 4

TROCAR SITE SUTURING DEVICE

This is a continuation-in-part of application Ser. No. 08/688,864 filed Jul. 31, 1996, now abandoned.

BACKGROUND OF THE INVENTION

1. Technical Field

The invention relates to the field of suturing surgical wounds and more particularly to hand-held devices to assist in the closure of trocar sites.

2. Background Art

Closing surgical sites, such as trocar sites, is well known in the surgical arts. Joining two surfaces or edges together, as may have been caused by surgery, and particularly endoscopic surgery, along a line by or as if by sewing has been done previously by physicians with devices such as mandibular awls and J-hooks.

Mandibular awls have been used to grasp the suture or thread and push the suture through the tissue lawyer on one side of the wound. The end of the suture is then withdrawn from the end of the awl, and the awl is then pushed through the desired tissue layer on the opposite side of the wound. The end of the suture is then replaced through the aperture in the end of the awl, and both the awl and the suture end are withdrawn from the body cavity. The physician can then secure or tie the loop of the suture.

As surgical techniques have improved with the reduction in size of surgical devices, the introduction of endoscopes, and the resulting decrease in the size of required openings into the body cavity, the techniques for closure of the surgical wounds has changed. Typical of this is form of modern surgery is endoscopic surgery, including laparoscopy and arthroscopy surgeries. In such small wound sites, often the physician cannot readily see either the tissue layer being sutured, such as the peritoneum in an abdominal wound, or the typical needle while it is being used for suturing. For such situations in which visualization is impaired, a J-hook can be used by insertion into the wound and penetration of the tissue layer for closure up from the interior of the body cavity on each side of the wound.

Also used with endoscopic surgery is a grasping device, such as an endoscopic forceps or an Endo Close disposable suturing device by Auto Suture Company, a division of United States Surgical Corp., of Norwalk, Conn. Such Endo Close device first traps a strand of the suture in the clasp or hooked end of the stylet. The suture is then pushed through the tissue layer into the body cavity or organ. The strand of the suture is then released and the Endo Close device is withdrawn. The Endo Close device is then pushed through the other side of the wound and the end of the suture is then trapped in the clasp end of the Endo Close device. The Endo Close device is then withdrawn and the suture is completed or tied. The endoscopic forceps are typically used in conjunction with the Endo Close device to hold the suture while the Endo Close device grasps the suture inside the body cavity.

While the above cited references introduce and disclose a number of noteworthy advances and technological improvements within the art, none completely fulfills the specific objectives achieved by this invention.

DISCLOSURE OF INVENTION

In accordance with the present invention, an apparatus for suturing wounds in a patient includes a first elongated hollow body having a bore extending therethrough. The hollow body has a first end that is adapted to receive a suturing element and a second end that is adapted to penetrate at least one tissue layer of the patient. A second elongated member similarly has a first end and a second end, which second end is adapted to penetrate at least one tissue layer of the patient. The second end of the second elongated member includes an aperture therethrough that is suitable for passing an end of the suture therethrough.

A first alignment device is disposed in proximity with the first end of the hollow body and a second, cooperating alignment device is similarly disposed in proximity with the first end of the second elongated member. The second end of the hollow body is formed with an exit face that is complementary to the aperture formed in the second elongated member such that the controlled joining of the first alignment device and the second alignment device holds the bore through the hollow body in alignment with the aperture through the second elongated body. The alignment of the first hollow body and the second elongated member when the first and second alignment devices are joined is such that an end of the suture can be introduced into the bore at the first end of the hollow body may pass completely through the bore exiting the bore at the second end of the hollow body, and then be communicated or pushed through the aperture that is formed in the second end of the elongated member.

The present invention is intended to aid in the closure of trocar sites and for endoscopic surgery, especially abdominal or laparoscopy, and obtaining hemostasis at the trocar sites. The present invention does not require visualization of the suture and can be done with "blind" techniques. Furthermore, the present trocar site suturing device is largely independent of operator's endoscopic surgical skill.

These and other objects, advantages and features of this invention will be apparent from the following description taken with reference to the accompanying drawings, wherein is shown the preferred embodiments of the invention.

BRIEF DESCRIPTION OF DRAWINGS

A more particular description of the invention briefly summarized above is available from the exemplary embodiments illustrated in the drawing and discussed in further detail below. Through this reference, it can be seen how the above cited features, as well as others that will become apparent, are obtained and can be understood in detail. The drawings nevertheless illustrate only typical, preferred embodiments of the invention and are not to be considered limiting of its scope as the invention may admit to other equally effective embodiments.

FIG. 1 is a side view of the two separated sections of the present invention penetrating a patient's wound shown in cross section.

FIG. 2 is a side view of the two sections of the present invention joined in alignment and having a suture threaded through the penetrating ends of each of the two sections.

FIG. 3 is a sectional view of the patient's wound with a strand of the suture after the present invention is removed from the wound.

FIG. 4 is one embodiment of the penetrating end of the tubular section of the present invention.

MODE(S) FOR CARRYING OUT THE INVENTION

Figure 5:
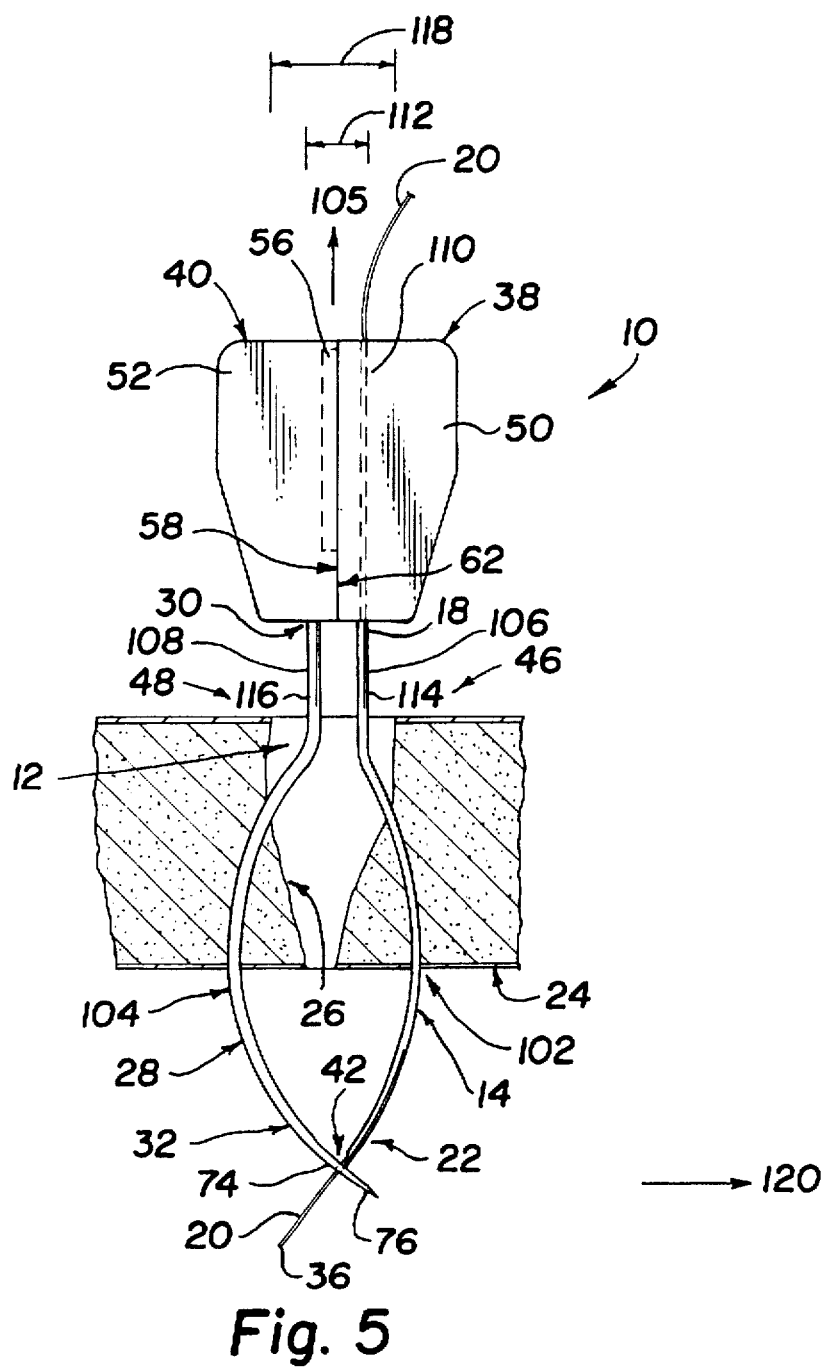
FIG. 5 is a side view of the two sections of a preferred alternative embodiment of the present invention joined in alignment and having opposing outwardly curved segments of the first elongated hollow body and the second elongated member.

So that the manner in which the above recited features, advantages and objects of the present invention are attained can be understood in detail, more particular description of the invention, briefly summarized above, may be had by reference to the embodiment thereof that is illustrated in the appended drawings. In all the drawings, identical numbers represent the same elements.

An apparatus 10 for suturing a wound or incision 12 in a patient includes a first elongated hollow body 14 having a bore 16 extending therethrough. The hollow body 14 has a first end 18 that is adapted to receive a strand of the suturing element or thread 20, and a second end 22 that is adapted to penetrate at least one tissue layer 24 or one wall 26 of the trocar site or incision 12 of the patient.

A second elongated member 28, such as a rigid awl-type extension, similarly has a first end 30 and a second end 32, which second end 32 is adapted to penetrate at least one tissue layer 24 or trocar site wall 26 of the patient. The second end 32 of the second elongated member 28 includes an aperture 34 therethrough that is suitable for passing an end 36 of the suture 20 therethrough. Generally, the second elongated element or member 28 includes a solid or hollow rod or cylinder section 72 and the second end 32 has a flat face portion 74 having a sharpened tip 76 with the aperture 32 therethrough.

A first alignment device 38 is disposed in proximity with the first end 18 of the hollow body 14 and a second, cooperating alignment device 40 is similarly disposed in proximity with the first end 30 of the second elongated member 28.

The second end 22 of the hollow body 14 is formed with an exit face 42 that is complementary to the aperture 34 formed in the second elongated member 28 such that the controlled joining of the first alignment device 38 and the second alignment device 40 holds the bore 16 through the hollow body 14 in alignment with the aperture 34 through the second elongated body or member 28. See FIG. 2. The alignment of the first hollow body 14 and the second elongated member 28 when the first and second alignment devices 38 and 40, respectively, are joined is such that an end 36 of the suture 20 can be introduced into the bore 16 at the first end 18 of the hollow body 14 and may pass completely through the bore 16 exiting the bore 16 through the hole 44 in the exit face 42 at the second end 22 of the hollow body 14, and then be communicated or pushed through the aperture 34 that is formed in the second end 32 of the second elongated member 28.

Preferably, the first alignment device 38 includes a handle portion 50 and the second alignment device 40 includes a handle portion 52. The corners of the handle portions 50 and 52 may be square or rounded for comfort, as desired. Indentations or bumps 54 may be formed in the gripping surfaces to improve the gripping ability of the handle or to reduce slippage. Alternatively, a plastic laminate layer may be attached or the handle may be formed from a non-slip type of plastic.

The second alignment device 40 may include a male finger 56 extending from a face 58 and the first alignment device 38 may be formed with a compatible female cavity 60 in face 62 that abuts face 58 when the first and second alignment devices 38 and 40 are joined.

The first hollow body 14 typically resembles a rigid medical needle element that is made from a metallic material or any suitable material that provides sufficient rigidity to the tubular element to reduce or prevent deformation of the first body 14 as the first and second alignment devices are joined and while the first element 14 is penetrating the tissue layer 24.

Preferably, the proximal or first end 18 of the needle or first hollow body 14 extends from the first alignment device 38 and has an enlarged opening to receive the first end 36 of the suture 20. The distal or second end 22 of the needle element 14 has a side-directed opening 44 that is formed similar to an end of an epidural needle to reduce the possibility of tissue coring as the needle penetrates the tissue layer 24. As is shown in FIG. 4, a scoop element or end 64 tends to block an direct contact of the opening 44 with the tissue layer. The exit face 42 is formed at an angle 66 to the longitudinal axis 66 of the needle 14 and is compatible with the face angle 70 of the second end 32 of the awl element 28 when the needle 14 and the awl element 28 are in the desired alignment with the first and second alignment devices 38 and 40 fitted together.

The suture or thread 20 may be of any known types, but preferably is sufficiently semi-rigid to be able to be pushed through the present invention 10.

Alternative Embodiment

In an alternative embodiment that is preferred for the typical use through a wound in relatively inelastic human skin, the first elongated hollow body includes a curved segment 102 towards the second end 22. Similarly, the second elongated member 28 may include a curved segment 104 towards the second end 32. It is desired that the curved portions or segments 102 and 104 are opposing and outwardly curved or bowed from each other and from a centerline 105 through the apparatus 10.

The opposing bowed or curved portions 102 and 104 are connected to the first and second alignment devices 38 and 40 or the handles 50 and 52, respectively, by straight segments or portions 106 and 108 to facilitate entry and maneuver within the hole or wound 12 through the skin. The distance 112 between the outside or outer walls 114 and 116 of the straight segments 106 and 108 of the needle bodies 14 and 28, respectively, is preferably not as wide as the typical width 118 of the surgical wound 12 to reduce stretching of the wound 12.

When the first alignment device 38 is controllably joined to the second alignment device 40, the straight segments 106 and 108 are essentially parallel. Further, when the first and second alignment devices 38 and 40 are joined, it is preferred that the curved first elongated hollow body 14 and the curved second elongated member 28 lie in a plane 120.

In such surgeries on humans, typically the skin is inelastic and one does not desire to increase the size of the wound; therefore, the shape of the alternative first elongated body and the second elongated member permits the surgeon to position the elongated bodies 14 and 28 through the wound 12 penetrating the wall of the wound and then joining in the viscera, such as the peritoneum.

The first end 36 of the suture 20 is introduced into the hollow first elongated body 14 through a passageway 110 formed in the handle 50 and is thread through the aperture in the second end 32 of the second elongated member 28. Completion of the surgical stitch is as described below.

Operation

The present invention 10 is used for suturing wounds 12 through at least one tissue layer 24 in a patient as follows.

The tissue layer 24 or the wall 26 of the trocar site in the patient is first penetrated in proximity to one side 46 of the wound 12 with the first elongated hollow body 14 having the bore 16 extending therethrough. The hollow body 14 has the first end 18 adapted to receive a suturing element 20 and a second end 22 adapted to penetrate at least one tissue layer 24 of the patient.

The tissue layer 24 or trocar site wall 26 on the opposite side 48 of the wound 12 from the location of penetration by the first hollow body 14 is then penetrated with the second elongated member 28 having a first end 30 and a second end 32 adapted to penetrate at least one tissue layer 24 of the patient. The second end 32 includes the aperture 34 therethrough that is suitable for passing the first end 36 of the suture 20 therethrough.

The first alignment device 38 that is disposed in proximity with the first end 18 of the first hollow body 14 is joined with the second, cooperating alignment device 40 that is disposed in proximity with the first end 30 of the second elongated member 28. See FIG. 2. The controlled joining of the first and second alignment devices 38 and 40, respectively, moves and holds the bore 16 through the hollow body 14 in alignment with the aperture 34 through the second elongated body 28.

The first end 36 of the suture or thread 20 is then introduced into the bore 16 at the first end 18 of the hollow body 14 and then the first end 36 of the suture 20 is moved or pushed through the length of the bore 16 to exit the bore 16 through the hole 44 at the second end 22 of the hollow body 44. Then the first suture end 36 is pushed further and communicated through the aperture 34 formed in the second end 32 of the second elongated member 28.

The first and second alignment devices 38 and 40, respectively, are then separated and the first elongated hollow body 14 and the second elongated member or awl-type extension 28 are both withdrawn from the tissue layers of the patient. The first end 36 of the suture 20 is pulled through the layer 24 of tissue being extended through aperture 34 of the second elongated member 28. See FIG. 3. The suture 20 is then tied.

Alternatively, the order of the first and second members 14 and 28, respectively, may be reversed as desired.

The foregoing disclosure and description of the invention are illustrative and explanatory thereof, and various changes in the size, shape and materials, as well as in the details of the illustrated construction may be made without departing from the spirit of the invention.

I claim:

1. An apparatus for suturing wounds in a patient comprising:
    a first elongated hollow body having a bore extending therethrough; the hollow body having a first end adapted to receive a suturing element and a second end adapted to penetrate at least one tissue layer of the patient;
    a second elongated member having a first end and a second end adapted to penetrate at least one tissue layer of the patient; the second end including an aperture therethrough suitable for passing an end of the suture therethrough;
    a first alignment device disposed in proximity with the first end of the hollow body and a second, cooperating alignment device disposed in proximity with the first end of the second elongated member; and
    the second end of the hollow body being formed with an exit face complementary to the aperture formed in the second elongated member such that the controlled joining of the first alignment device and the second alignment device holds the bore through the hollow body in alignment with the aperture through the second elongated body such that an end of the suture introduced into the bore at the first end of the hollow body may pass through the bore and exit the bore at the second end of the hollow body, and then be communicated through the aperture formed in the second end of the elongated member.

2. The invention of claim 1 wherein the first elongated hollow body is rigid to resist deformation from the penetration of the tissue layer as the first alignment device and the second alignment device are joined together.

3. The invention of claim 1 wherein the suture is semi-rigid.

4. The invention of claim 1 wherein the second alignment device includes a male finger and the first alignment device includes a compatible female cavity to receive the male member of the second alignment device.

5. The invention of claim 1 wherein the first alignment device includes a handle and the second alignment device includes a handle.

6. The invention of claim 5 wherein the handle of the first alignment device and the handle of the second alignment device include slip reducing surfaces.

7. The invention of claim 1 wherein the second end of the hollow body includes a side directed opening to reduce coring.

8. The invention of claim 1 wherein the second elongated member is a rod and the second end of the second elongated member is formed having a flat face with the aperture therethrough.

9. The invention of claim 1 wherein the first alignment device includes a handle and the second alignment device includes a handle.

10. The invention of claim 1 wherein the second end of the first elongated hollow body includes a segment that is outwardly curved from a centerline through the apparatus.

11. The invention of claim 1 wherein the second end of the second elongated member includes a segment that is outwardly curved from a centerline through the apparatus.

12. The invention of claim 10 wherein the first elongated hollow body further includes a straight portion extending between the curved segment of the second end of the first elongated hollow body and the first alignment device.

13. The invention of claim 11 wherein the second elongated member further includes a straight portion extending between the curved segment of the second end of the second elongated member and the second alignment device.

14. The invention of claim 1 wherein the second end of the first elongated hollow body includes a segment that is outwardly curved from a centerline through the apparatus; the second end of the second elongated member includes a segment that is outwardly curved from a centerline through the apparatus; the first elongated hollow body further includes a straight portion extending between the curved segment of the second end of the first elongated hollow body and the first alignment device; the second elongated member further includes a straight portion extending between the curved segment of the second end of the second elongated member and the second alignment device; and, the first elongated hollow body straight segment and the second elongated member straight segment are essentially parallel when the first alignment device is controllably joined to the second alignment device.

15. An method for suturing wounds through at least one tissue layer in a patient comprising:
    penetrating the tissue layer of the patient in proximity to one side of the wound with a first elongated hollow body having a bore extending therethrough; the hollow body having a first end adapted to receive a suturing element and a second end adapted to penetrate at least one tissue layer of the patient;

penetrating the tissue layer opposite side of the wound from the location of penetration by the first hollow body with a second elongated member having a first end and a second end adapted to penetrate at least one tissue layer of the patient; the second end including an aperture therethrough suitable for passing an first end of the suture therethrough;

then joining a first alignment device disposed in proximity with the first end of the hollow body with a second, cooperating alignment device disposed in proximity with the first end of the second elongated member such that the controlled joining of the first alignment device and the second alignment device holds the bore through the hollow body in alignment with the aperture through the second elongated body;

introducing the first end of the suture into the bore at the first end of the hollow body; moving the first end of the suture through the bore to exit the bore at the second end of the hollow body, and then communicating the first suture end through the aperture formed in the second end of the elongated member;

separating the first and second alignment devices; and withdrawing the first elongated hollow body and the second elongated member from the tissue layer of the patient pulling the first end of the suture through the layer of tissue with the second elongated member.

16. The invention of claim 15 wherein the first elongated hollow body is rigid to resist deformation from the penetration of the tissue layer as the first alignment device and the second alignment device are joined together.

17. The invention of claim 15 wherein the suture is semi-rigid.

18. The invention of claim 15 wherein the second alignment device includes a male finger and the first alignment device includes a compatible female cavity to receive the male member of the second alignment device.

19. The invention of claim 15 wherein the second end of the hollow body includes a side directed opening to reduce coring.

20. The invention of claim 15 wherein the second elongated member is a rod and the second end of the second elongated member is formed having a flat face with the aperture therethrough.

21. The invention of claim 15 wherein the first alignment device includes a handle and the second alignment device includes a handle.

22. The invention of claim 15 wherein the second end of the first elongated hollow body includes a segment that is outwardly curved from a centerline through the apparatus.

23. The invention of claim 15 wherein the second end of the second elongated member includes a segment that is outwardly curved from a centerline through the apparatus.

24. The invention of claim 22 wherein the first elongated hollow body further includes a straight portion extending between the curved segment of the second end of the first elongated hollow body and the first alignment device.

25. The invention of claim 23 wherein the second elongated member further includes a straight portion extending between the curved segment of the second end of the second elongated member and the second alignment device.

26. The invention of claim 15 wherein the second end of the first elongated hollow body includes a segment that is outwardly curved from a centerline through the apparatus; the second end of the second elongated member includes a segment that is outwardly curved from a centerline through the apparatus; the first elongated hollow body further includes a straight portion extending between the curved segment of the second end of the first elongated hollow body and the first alignment device; the second elongated member further includes a straight portion extending between the curved segment of the second end of the second elongated member and the second alignment device; and, the first elongated hollow body straight segment and the second elongated member straight segment are essentially parallel when the first alignment device is controllably joined to the second alignment device.

* * * * *